United States Patent [19]

Kiyuna

[11] Patent Number: 6,073,040
[45] Date of Patent: Jun. 6, 2000

[54] ELECTROPHYSIOLOGICAL ACTIVITY ESTIMATION METHOD

[75] Inventor: Tomoharu Kiyuna, Tokyo, Japan

[73] Assignee: NEC Corporation, Tokyo, Japan

[21] Appl. No.: 09/009,252

[22] Filed: Jan. 20, 1998

[30] Foreign Application Priority Data

Jan. 20, 1997 [JP] Japan ..................................... 9-019619

[51] Int. Cl.$^7$ ....................................................... A61B 5/05
[52] U.S. Cl. .......................................... 600/409; 600/544
[58] Field of Search .................................... 600/407, 409, 600/544, 545

[56] References Cited

U.S. PATENT DOCUMENTS

| | | | |
|---|---|---|---|
| 5,263,488 | 11/1993 | Van Veen et al. | 600/544 |
| 5,361,774 | 11/1994 | Yamazaki et al. | 600/405 |
| 5,392,210 | 2/1995 | Scholz | 600/407 |
| 5,417,211 | 5/1995 | Abraham-Fuchs et al. | 600/409 |
| 5,730,131 | 3/1998 | Ohyu | 600/544 X |
| 5,797,853 | 8/1998 | Musha et al. | 600/544 |

FOREIGN PATENT DOCUMENTS

| | | |
|---|---|---|
| 3-277345 | 12/1991 | Japan . |
| 4-8347 | 1/1992 | Japan . |
| 6-121776 | 5/1994 | Japan . |
| 6-311975 | 11/1994 | Japan . |
| 6-343613 | 12/1994 | Japan . |
| 6-343614 | 12/1994 | Japan . |
| 8-299295 | 11/1996 | Japan . |
| 9-56688 | 3/1997 | Japan . |
| 9-66038 | 3/1997 | Japan . |

OTHER PUBLICATIONS

H. Yamashita et al., "Nonlinear Programming", *Science Technology Assn. of Japan*, pp. 146–148, (1987).

Vapnik, "The Nature of Statiscal Learning Theory", Springer, New York, pp. 72–74, (1995).

Rissanen, "Modeling by Shortest Data Description", *Automatica*, vol. 14:465–471, (1978).

Ishiguro, "Information Theoretical Statistics", *Kyoritsu Publication Co. of Japan*, pp. 42–43, (1983).

*Primary Examiner*—Francis J. Jaworski
*Attorney, Agent, or Firm*—Foley & Lardner

[57] ABSTRACT

An electrophysiological activity estimation method is used to estimate active areas of a selected part of a living body (e.g., human brain). Based on electromagnetic field distribution measured on a surface of the selected part of the living body as well as its shape, the method assumes each equivalent current dipole as a source of electromagnetic field distribution. At first, grid points are created to cover the selected part of the living body (e.g., head). Using the pseudoinverse, the method performs estimation of dipole distribution for equivalent current dipoles. Then, the equivalent current dipoles are subjected to sorting based on a priority order. An evaluation function (e.g., structural risk) is calculated in accordance with a square error between the measured electromagnetic field distribution and a theoretical value of electromagnetic field distribution caused by the equivalent current dipole, as well as a number of measuring points and a number of equivalent current dipoles. Estimation and calculations are repeated while changing a number of equivalent current dipoles in accordance with the priority order. Then, noise distribution is estimated in response to a minimum value of the evaluation function. So, the dipole distribution is estimated using the noise distribution. Thus, it is possible to obtain estimation results which are represented by a direction and magnitude of the equivalent current dipole as well as an appropriate number of equivalent current dipoles.

19 Claims, 5 Drawing Sheets

ELECTROPHYSIOLOGICAL ACTIVITY ESTIMATION METHOD

BACKGROUND OF THE INVENTION

1. Field of the Invention

This invention relates to electrophysiological activity estimation methods which estimate equivalent current dipoles (i.e., ECD) based on the electromagnetic field distribution which is measured on a surface of a living body such as a scalp of a human. This invention is based on patent application No. Hei 9-19619 filed in Japan, the content of which is incorporated herein by reference.

2. Prior Art

Conventionally, the equivalent current dipole estimation method is known as the method to estimate active areas of a human brain on the basis of electromagnetic field distribution measured on a scalp of a human. By observing active areas of the human brain, it is possible to obtain information with regard to high-order functions of the brain as well as diseased parts of the brain.

Now, a general method to calculate an equivalent current dipole will be described with respect to estimation of active areas of the brain. When a nerve cell (or neuron) of the brain is excited by an impulse (or stimulus) given thereto from an external device, pulse-like current flows across a connection (or axon) connecting neurons together. Due to occurrence of the current, weak electromagnetic field is caused to occur around a scalp of the human. A source of the electromagnetic field is subjected to modeling using current elements called equivalent current dipoles (simply called "dipoles"). By estimating six parameters of the dipole, it is possible to estimate an active area of the human brain. Herein, the six parameters contain three parameters for designation of an area, two parameters for designation of a direction and one parameter for representation of magnitude (or intensity) with respect to the dipole.

Two methods are known as the method to estimate the parameters of the dipole. Herein, the six parameters of the dipole are unknown while a measured value of the electromagnetic field is represented by an equation as follows:

$$y = (y_1, y_2, \ldots, y_n)^T \qquad \text{[Equation 1]}$$

A theoretical value is calculated using the dipole model represented by an equation as follows:

$$f(\theta_j) = (f_1(\theta_j), f_2(\theta_j), \ldots, f_n(\theta_j))^T. \qquad \text{[Equation 2]}$$

So, a square residual is calculated as follows:

$$E = \sum_{i=1}^{n} \left[ y_i - \sum_{j=1}^{m} f_i(x_i, \theta_j) \right]^2 \qquad \text{[Equation 3]}$$

The aforementioned method estimates the parameter minimizing the square residual, which is represented by an equation as follows:

$$\theta_j = (x_j', e_j, q_i)^T \qquad \text{[Equation 4]}$$

In the aforementioned equations, "n" denotes a number of measuring points; "m" denotes a number of dipoles; "$y_i$" denotes a measured value of the electromagnetic field measured at a measuring point i; "$f_i$" denotes a theoretical value of the electromagnetic field at the measuring point i. In addition, a vector corresponding to combination of the measured value and theoretical value of the electromagnetic field is represented as follows:

$$y, f$$

Incidentally, an expression of $(\ldots)^T$ represents the transposition. Further, a coordinate of the measuring point i is represented by $$x_i$$

while a dipole parameter at the measuring point j is represented by an equation as follows:

$$\theta_j = (x_j', e_j, q_i)^T \qquad \text{[Equation 5]}$$

In addition, the position, direction and magnitude of the dipole at the measuring point j are respectively represented by symbols as follows:

$$x_j', e_j, q_j$$

As the method to estimate the foregoing dipole parameters, it is possible to use the nonlinear optimization algorithms such as the Levenberg-Marquardt method and simplex method. Details of the nonlinear optimization algorithms are shown by "paper 1" which is a book entitled "Nonlinear Programming" which is written by Mr. Hiroshi Yamashita and Mr. Hiroshi Konno and is provided by Science Technology Association of Japan on 1987, for example. Further, the method using the pseudoinverse of the matrix (or Moore-Penrose inverse) is known as an example of the other methods for the current dipole estimation, especially as an example of the estimation method for "distributed" active areas of the living body. According to this method, the theoretical equation of the electromagnetic field is represented as follows:

$$f_i = \sum_{j=1}^{m} q_i F(x_i, x_j', e_j). \qquad \text{[Equation 6]}$$

So, it is possible to use the characteristic of the above equation that elements regarding the magnitude of the dipole are coordinated by the linear function. Concretely speaking, the shape of the brain is approximated by the set of the polyhedrons while the position and direction of the dipole are fixedly located on the polyhedron, so that the magnitude $q_i$ of the dipole is calculated as an unknown parameter. In this case, the function of "F" is represented by the matrix, so the aforementioned equation 6 is rewritten in the matrix form as follows:

$$f = Fq \qquad \text{[Equation 7]}$$

For example, the electroencephalograph (i.e., EEG which represents a brain wave measuring instrument) is used to measure the electric field distribution (or electric potential distribution), based on which the dipole is estimated. In this case, calculation for F is made with regard to elements i, j in accordance with an equation as follows:

$$F_{ij} = \frac{1}{4\pi} \sum_{n,m} \frac{Y_{nm}(\vartheta_i, \phi_i)}{\|Y_{nm}(\vartheta_i, \phi_i)\|} e_j \cdot \nabla' R(r_i, r_j') Y_{nm}'(\vartheta_j', \phi_j') \qquad \text{[Equation 8]}$$

In the above equation, "Y" denotes the spherical harmonics; symbols r,θ,φ show the position of the measuring point in polar coordinates while symbols r',θ',φ' show the position of the dipole in polar coordinates. A symbol $\nabla'$ denotes a differential operator while a mathematical expression of R(r,r') corresponds to the function regarding r and r', which is determined by the boundary condition. Using a SQUID (an abbreviation for "Superconducting Quantum Interference Device"), it is possible to measure the magnetic field distribution, based on which the dipole is estimated in accordance with an equation as follows:

$$F_{ij} = \frac{\mu_0}{4\pi} \frac{n_i \cdot e_j \times (x_i - x'_j)}{\|x_i - x'_j\|} \qquad \text{[Equation 9]}$$

where $\mu_0$ is a magnetic permeability. In addition, $n_i$ denotes a normal vector with respect to a surface of a head model at a measuring point i. A square error is represented by an equation as follows:

$$E = \|y - Fq\|^2 \qquad \text{[Equation 10]}$$

Herein, a vector q which minimizes the above square error is represented, using a pseudoinverse $F^+$ of F, by an equation as follows:

$$q = F^+ y \qquad \text{[Equation 11]}$$

The dipole estimation method using the pseudoinverse is disclosed by "paper 2" corresponding to Japanese Patent Laid-Open Publication No. 6-343613 as well as "paper 3" corresponding to Japanese Patent Laid-Open Publication No. 6-343614, for example.

Figure 6:
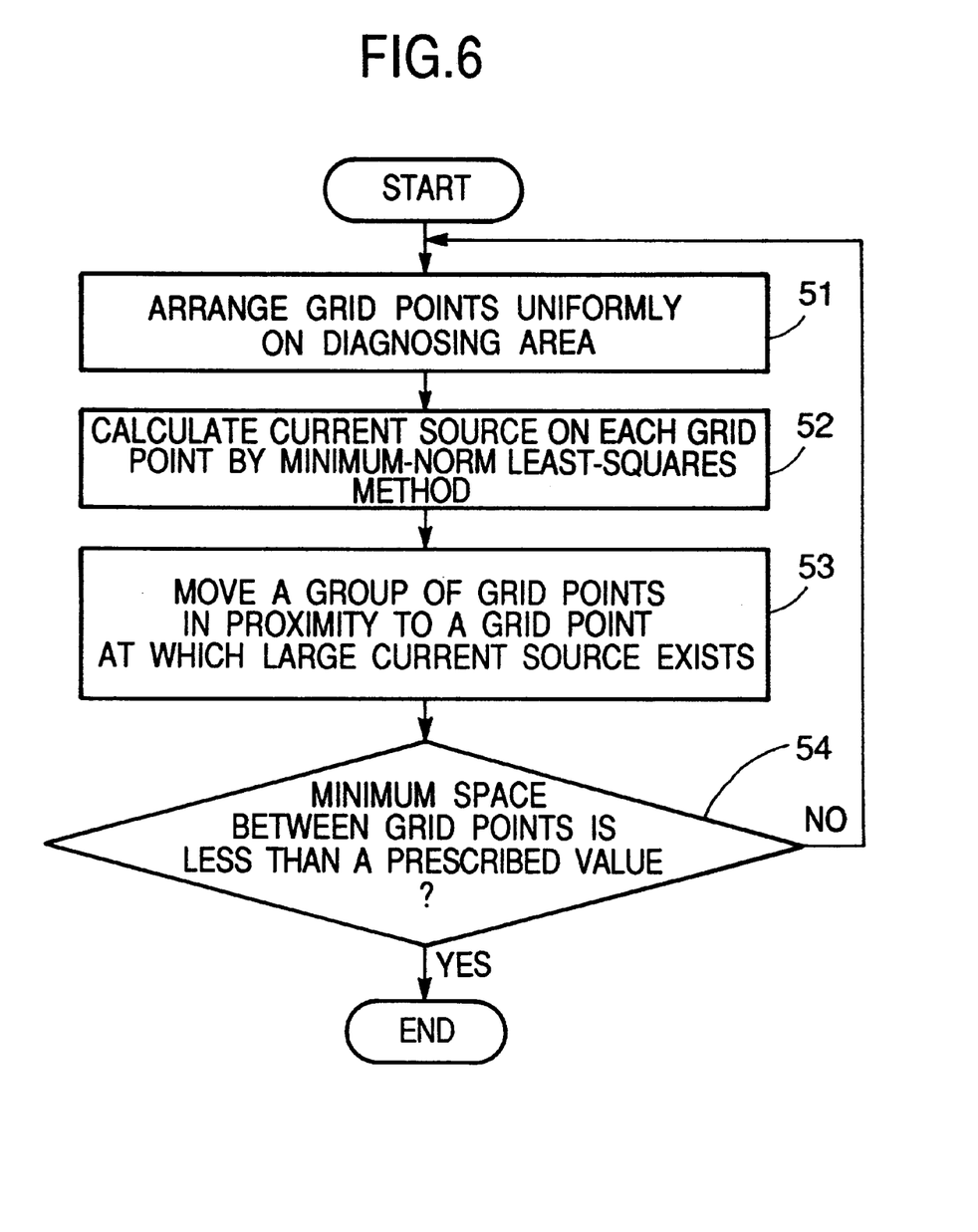
FIG. 6 is a flowchart showing procedures of the conventional dipole estimation method using the pseudoinverse.

Now, FIG. 6 is a flowchart showing an example of processing which the conventional system executes in accordance with the conventional method using the pseudoinverse. First, a group of grid points are arranged uniformly with respect to a diagnosing area, i.e., an area on which active areas are estimated in step 51. In step 52, a current source is calculated with regard to each of the grid points in accordance with the minimum-norm least-squares method. In step 53, a group of grid points are moved in proximity to a grid point on which a current source having a large value exists. Then, a minimum space between grid points is selected from among spaces between the grid points. In step 54, a decision is made as to whether the minimum space is less than a prescribed value or not. If the minimum space is less than the prescribed value, the system completes the proceeding of FIG. 6 because the convergence is obtained. If not, the system proceeds back to step 51.

According to the aforementioned method, the system performs estimation while changing the distance between the grid points in order to improve a precision of estimation. However, the conventional system does not perform estimation with respect to a number of dipoles. In addition, the conventional system is not designed to cope with problems due to the noise.

Next, a description will be given with respect to problems which the conventional dipole estimation method suffers from.

Figure 7:
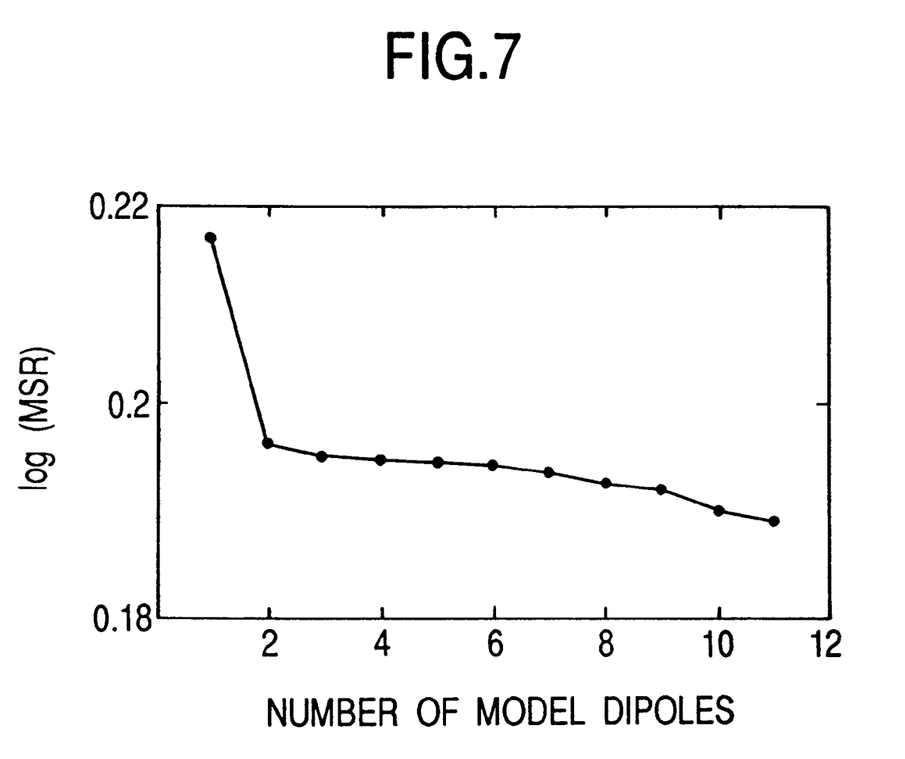
FIG. 7 is a graph showing a relationship between a number of model dipoles and a square error with respect to the conventional dipole estimation method using the nonlinear optimization algorithm.

Normally, the method using the nonlinear optimization algorithm uses one to three dipoles to perform estimation of an active area. However, it is impossible to know a number of the active areas in the brain in advance. For this reason, there are provided dipole models whose number of dipole(s) is one, two and three respectively, for example. Using the dipole models, the system performs the estimation. So, the system employs the best result of the estimation. In this case, a square error E can be used as an element of evaluation criterion for the quality of estimation. However, there is a tendency that the square error becomes smaller as a number of dipoles is increased more. For this reason, there is a problem that a number of dipoles cannot be detected with accuracy. FIG. 7 shows an example of variations of the square error of the estimation which is made with respect to the magnetic field distribution produced by two dipoles while changing a number of model dipole(s) from one to eleven. In FIG. 7, the vertical axis corresponds to the logarithmic notation of the mean square error (or mean square residual, i.e., MSR) while the horizontal axis represents a number of model dipoles. According to the graph of FIG. 7, it is observed that the square error is decreased as a number of model dipoles is increased. So, if the square error is used as the evaluation criterion, although a true number of dipoles is two, the best result of the estimation is obtained with respect to the case of eleven model dipoles. This is a wrong result. In addition, the method using the nonlinear optimization algorithm requires a long time to perform the estimation one time. Further, it is necessary to perform the estimation several times while changing the number of the dipoles. Namely, the conventional method requires a large load to calculations as well as a long time for the estimation.

Another conventional method using the pseudoinverse arranges several hundreds to 10,000 dipoles with regard to each element of the polyhedrons approximating the shape of the brain, wherein magnitude of each dipole is calculated. According to this method, the estimation can be made using multiplication of matrix only. So, this method requires a short time for the estimation. Even if a neural activity lies in an extended area, the method is capable of providing information about the size of the area. The method using the pseudoinverse is designed to use the linear model. For this reason, this method has a drawback corresponding to weakness against the noise.

Now, a description will be given with respect to reasons why the method using the pseudoinverse has such a drawback.

Using the singular value decomposition (i.e., SVD), the pseudoinverse $F^+$ is written by an equation as follows:

$$F^+ = V \wedge U^T = \sum_{\lambda_i > 0} \frac{1}{\lambda_i} v_i u_i^T \qquad \text{[Equation 12]}$$

where $u_i, v_i$ represent column vectors i for matrices U, V; $\lambda_i$ represents a singular value of the matrix F, so sum is performed with respect to singular values which are not zero. If measurement data do not contain noise, correct dipole distribution can be obtained by multiplication of the pseudoinverse and measurement data in accordance with an equation as follows:

$$q = F^+ y = \sum_{\lambda_i > 0} \frac{1}{\lambda_i} v_i (u_i^T \cdot y) \qquad \text{[Equation 13]}$$

where q corresponds to a solution vector having a minimum norm which minimizes the square error. However, in the case where the measurement data contain noise z, the equation 13 should be rewritten by using an equation as follows:

$$y = y_0 + z \qquad \text{[Equation 14]}$$

where $y_0$ corresponds to measurement data containing no noise. So, using the equation 14, the equation 13 is rewritten as follows:

$$q = F^+ y = F^+(y_0 + z) = \sum_{\lambda i > 0} \frac{1}{\lambda i} v_i(u_i^T \cdot y_0) \qquad \text{[Equation 15]}$$
$$+ \sum_{\lambda i > 0} \frac{1}{\lambda i} v_i(u_i^T \cdot y)$$

In the above equation, a second term of the right side shows an extremely large value with respect to a small singular value λi. So, the divergence occurs on an estimated value of the magnitude of the dipole.

So, the problems of the conventional methods can be summarized as follows:

In the case of the method using the nonlinear optimization algorithm where the square error is used as the evaluation criterion for the estimation, it is impossible to estimate a number of dipoles. In the case of the method using the pseudoinverse for estimation of the distributed active area, the divergence occurs on estimation of the magnitude of the dipole due to the effect of the noise.

SUMMARY OF THE INVENTION

It is an object of the invention to provide an electrophysiological activity estimation method for estimation of active areas of a living body (or organism) which is capable of estimating a number of dipoles with accuracy and which is capable of performing noise-robust estimation of the dipoles.

According to an aspect of this invention, an electrophysiological activity estimation method is applied to estimation of active areas of a selected part of a living body (e.g., human brain). Herein, each current dipole is assumed as a source of electromagnetic field distribution on the basis of measured electromagnetic field distribution measured on the human scalp as well as its shape.

At first, grid points are created to cover the selected part of the living body (e.g., head). Using the pseudoinverse, the method performs estimation of dipole distribution for equivalent current dipoles. Then, the equivalent current dipoles are subjected to sorting based on a priority order. An evaluation function (e.g., structural risk) is calculated in accordance with a square error between the measured electromagnetic field distribution and a theoretical value of electromagnetic field distribution caused by the equivalent current dipole, as well as a number of measuring points and a number of equivalent current dipoles.

The above estimation and calculations are repeated while changing a number of equivalent current dipoles in accordance with the priority order. Then, noise distribution is estimated in response to a minimum value of the evaluation function. So, the dipole distribution is estimated using the noise distribution. Thus, it is possible to obtain estimation results which are represented by the direction and magnitude of the equivalent current dipole as well as an appropriate number of equivalent current dipoles.

By changing the number of equivalent current dipoles as a repetition of the estimation and calculations, it is possible to change a group of equivalent current dipoles used for the estimation. In other words, after performing the estimation using the pseudoinverse, this invention excludes unnecessary dipoles which are regarded as "fake" neural activities. Therefore, as compared with the conventional methods, the electrophysiological activity estimation method of this invention is advantageous that equivalent current dipole estimation can be performed with a small amount of calculations and at a high speed.

In addition, by using the noise distribution for the estimation of the dipole distribution, this invention is capable of constructing an architecture of processing for the dipole estimation which is robust against the noise.

BRIEF DESCRIPTION OF THE DRAWINGS

These and other objects of the subject invention will become more fully apparent as the following description is read in light of the attached drawings wherein.

DESCRIPTION OF THE PREFERRED EMBODIMENT

Before describing the preferred embodiment of this invention, a description will be given with respect to a principle of the invention.

This invention is characterized by introducing a new evaluation function "L" which is used instead of the square error used by the conventional methods. Herein, the evaluation function L is established in consideration of the complexity of the models. According to an example of the evaluation function, for example, the complexity of the model is evaluated using a number of parameters (i.e., a number of dipoles), wherein an excessive use of parameters is prohibited. Concretely speaking, a structural risk is used as an evaluation function $L_{SRM}$. The structural risk is defined by equations as follows:

$$L_{SRM} = \frac{E}{C_{SRM}} \qquad \text{[Equation 16]}$$

$$C_{SRM} = 1 - c \sqrt{\frac{d_{vc}(m)\left\{\log\left[\frac{2n}{d_{vc}(m)}\right] + 1\right\} + \log 4\eta}{n}}$$

where E denotes a square error between a measured value and a theoretical value of electromagnetic field distribution; n denotes a number of measuring points while m denotes a number of dipole parameters (i.e., a number of dipoles). In addition, η is a value regarding a probability, so the above equation is established with a probability of 1−η. Further, $d_{VC}(m)$ is called a Vapnik-Chervonenkis (VC) dimension which corresponds to the quantity used as an index of the diversity or expressiveness of the model. Therefore, the VC dimension becomes large together with a number of parameters of the model. In addition, $C_{SRM}$ which is used as a denominator of the above equation becomes small, so a value of $L_{SRM}$ as a whole becomes large.

This invention is designed to determine that an optimum model corresponds to a dipole model which minimizes the new evaluation criterion of $L_{SRM}$. The conventional method suffers from a problem that a true number of dipoles cannot be estimated because a square error becomes small as a number of parameters of the model becomes large. In contrast, this invention uses the evaluation function $L_{SRM}$, according to which $C_{SRM}$ becomes small together with a number of dipole parameters. So, an excessive use of parameters brings a disadvantage in an aspect of minimization of $L_{SRM}$. According to the mechanism of the invention described above, it is possible to estimate a number of dipoles. In the new evaluation function $L_{SRM}$ can be assumed as a penalty term which acts to prohibit the excessive use of parameters. Incidentally, details of the theoretical basis that the evaluation function $L_{SRM}$ is effective for estimation of a number of dipoles is provided by "paper 4" which corresponds to V. N. Vapnik, "The Nature of Statistical Learning Theory", Springer, N.Y., 1995.

Other than the aforementioned evaluation function represented by the equation 16, this invention is capable of employing an evaluation function based on a description length $L_{MDL}$, for example. In addition, it is possible to use the Akaike information criterion $L_{AIC}$ as the evaluation function. Incidentally, the evaluation function based on $L_{MDL}$ can be assumed as a simplified form of the aforementioned evaluation function of the equation 16.

If the conventional methods, especially the method using the nonlinear optimization algorithm, use the equation 16 which allows estimation of a number of dipoles as the evaluation function, it is necessary to perform estimation many times while changing the number of model dipoles, and it is necessary to perform comparison of an evaluated value of $L_{SRM}$ with respect to each estimation. For this reason, there is a problem that much time is required for the estimation. In contrast to the conventional methods, this invention is designed to perform estimation procedures as follows:

At first, estimation is performed using the pseudoinverse with respect to dipole distribution. Then, estimation is performed with respect to a number of dipoles while deleting unnecessary dipoles from the dipole distribution or adding dipoles having a high priority order to the dipole distribution. The method using the pseudoinverse is capable of performing dipole estimation by using multiplication of matrices only. So, as compared with the method using the nonlinear optimization algorithm which requires iterative calculations, the method using the pseudoinverse is capable of estimating a number of dipoles in a short period of time. Incidentally, the concrete content of method using the pseudoinverse can be summarized as follows:

Singular value decomposition is performed on matrices which are determined by position information of equivalent current dipoles as well as arrangement of measuring points of electromagnetic field distribution. Using information representing a singular value, the method performs estimation of the equivalent current dipoles with respect their directions and magnitude.

There is a property that a square error at a time when the aforementioned $L_{SRM}$ becomes minimal is equivalent to magnitude of noise distribution. Using such a property, it is possible to improve noise resistance with regard to the dipole estimation method using the pseudoinverse. Concretely speaking, the sum of the aforementioned equation 13 is subjected to limitation that the square error is equivalent to the noise distribution. In other words, the equation 13 is rewritten as follows:

$$q = F^+ y = \sum_{E \geq \|z\|} \frac{1}{\lambda i} v_i(u_i^T \cdot y) \qquad \text{[Equation 17]}$$

where $\|z\|$ is estimated magnitude of the noise distribution. By changing the content of the sum as described above, this invention is capable of avoiding over-fitting to the noisy data, so it is possible to realize the noise-robust estimation. In this case, singular value decomposition is performed on matrices which are determined by position information of equivalent current dipoles as well as arrangement of measuring points of electromagnetic field distribution. Thus, using the noise distribution as well as error information, it is possible to perform estimation with respect to directions and magnitude of the equivalent current dipoles, for example.

Incidentally, there are two methods for determination of the aforementioned priority order, as follows:
  i) The priority order is determined to coincide with an order of absolute values of the equivalent current dipoles.
  ii) An error is detected between measured electromagnetic field distribution and electromagnetic field distribution which is caused by each equivalent current dipole. So, the priority order is determined to coincide with an order of errors.

Figure 1:
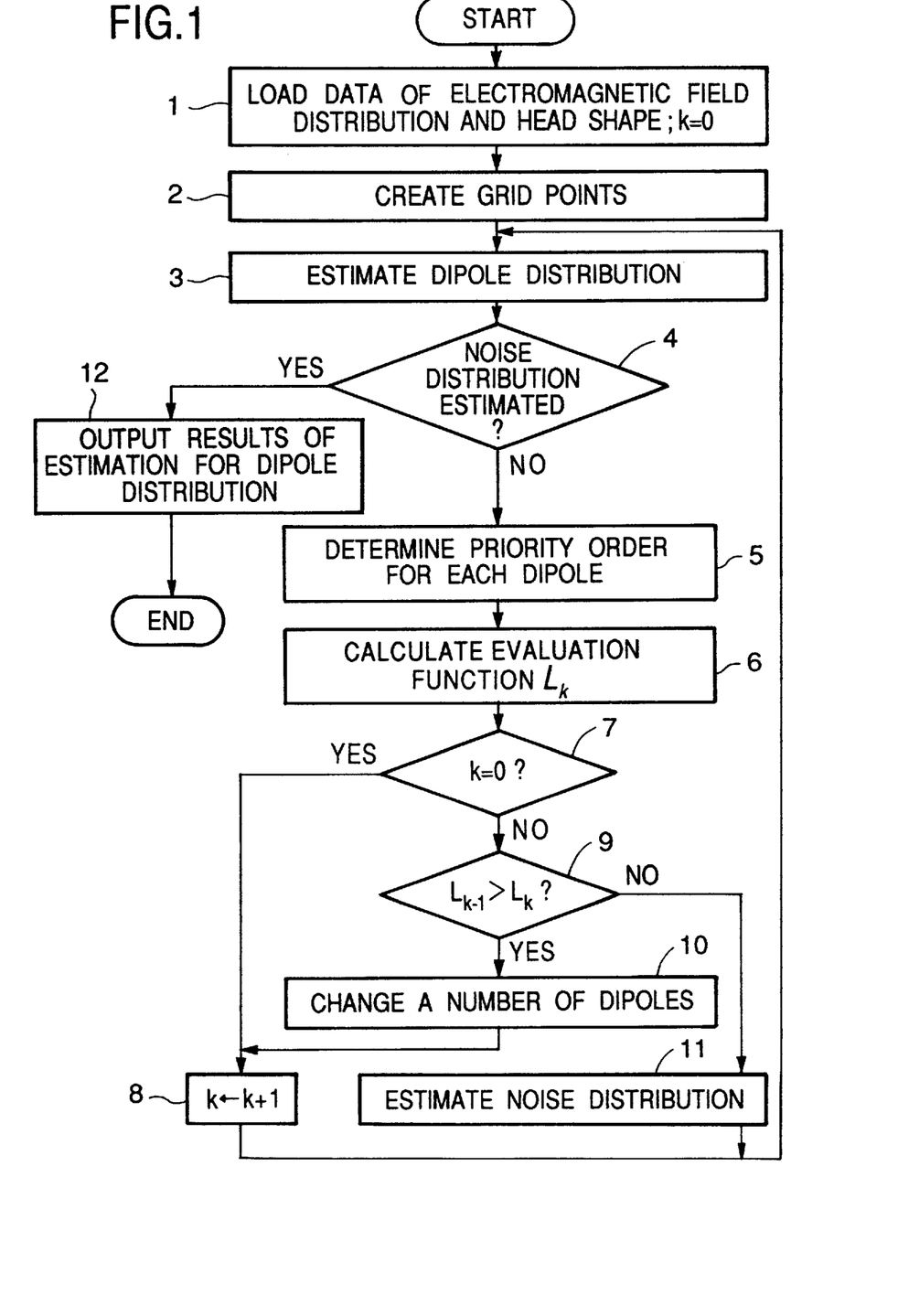
FIG. 1 is a flowchart showing procedures of an electrophysiological activity estimation method in accordance with an embodiment of the invention.
Figure 2:
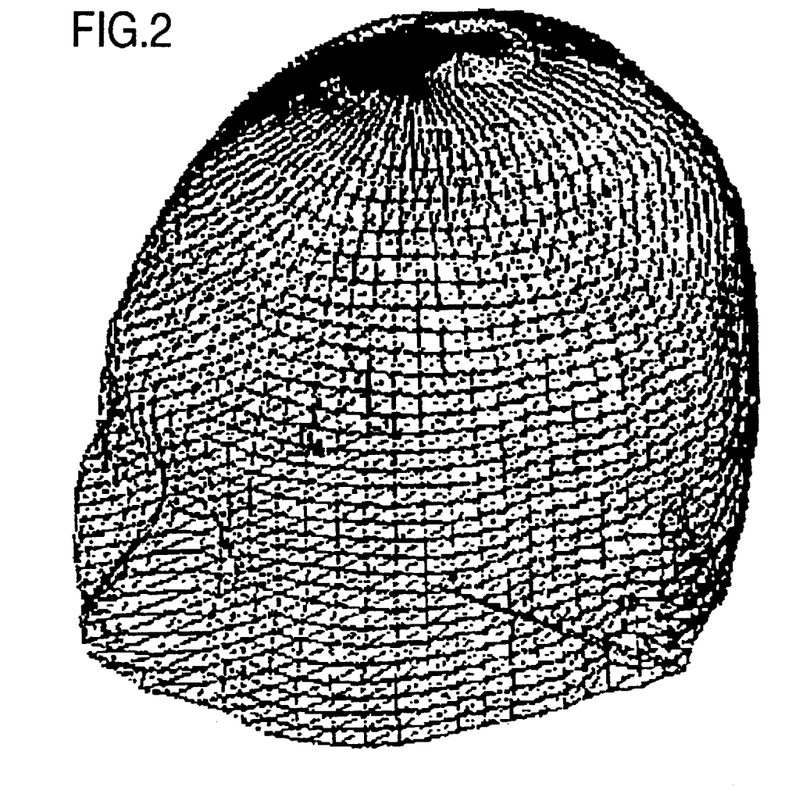
FIG. 2 shows an example of a shape of a human head which is approximated using polyhedrons.

Next, a description will be given with respect to the preferred embodiment of the present invention. FIG. 1 is a flowchart showing concrete procedures to execute an electrophysiological activity estimation method in accordance with one embodiment of the invention. Incidentally, the embodiment refers to the method to estimate active areas of a brain on the basis of electromagnetic field distribution measured on a scalp of a living body called "subject". However, this invention is not limited to such estimation of the active areas of the brain. For example, the method similar to the method of this invention can be employed for estimation of active areas of a heart on the basis of measured electromagnetic field distribution which is measured on the breast of the subject. In addition, this invention can be applied to estimation of active areas of the digestive organ and muscle as well.

In step 1 of the flowchart of FIG. 1, a loop counter variable k is subjected to initial setting at '0'. In addition, the system of this invention loads data regarding electromagnetic field distribution measured at 'n' measuring points on a head of a subject. Further, the system loads data regarding a shape of the head of the subject. As for measurement of the electromagnetic field distribution, an electroencephalograph (i.e., EEG) is used with respect to measurement of electric field distribution (i.e., brain waves) while a SQUID is used with respect to measurement of magnetic field distribution. Normally, 20 to 150 measuring points are located on the scalp of the subject. At the measurement, the system records coordinates of the measuring points as well as reference points of the head, for example, the nasion (i.e., the intersection of the internasal suture with the nasofrontal suture in the midsagittal plane) as well as the left and right ears, etc. Incidentally, measurement of the shape of the head is performed using the equipment of MRI (an abbreviation for "Magnetic Resonance Imaging") or X-ray CT scanner (where "CT" is an abbreviation for "Computed Tomography"), for example. Instead of using an actual shape of the head, it is possible to use an approximated model that approximates the head as a sphere, for example. Using such a sphere model may bring a small reduction in precision of estimation, however, there is an effect that load of calculations can be reduced.

Figure 3:
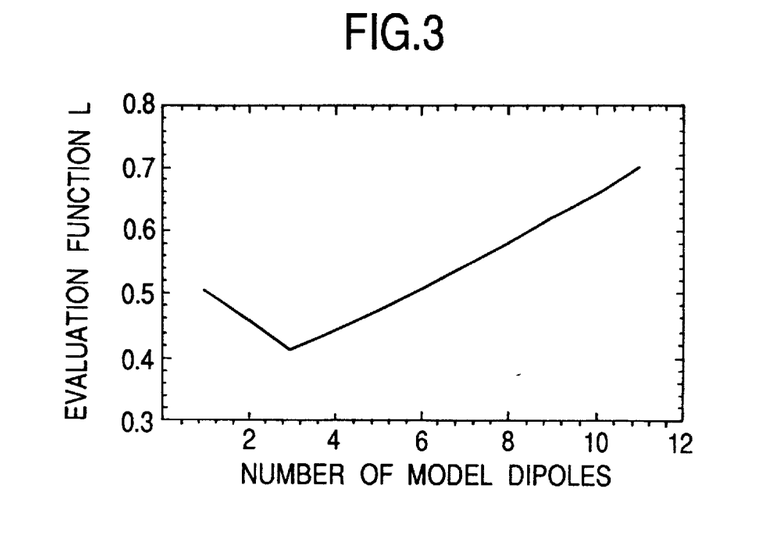
FIG. 3 is a graph showing a relationship between a value of an evaluation function and a number of model dipoles.

In step 2, the shape of the head of the subject is approximated using polyhedrons (e.g., a set of triangles) on the basis of head shape data which are read into the system in step 1. Thus, the system creates grid points. FIG. 3 shows an example of a head model corresponding to an approximated shape of the head using a set of triangles. This head model is reconstructed from a set of MRI pictures of the head. As an active area model of the brain, a unit dipole having magnitude of 1.0 is located inside of each triangle. Herein, a number of model dipoles is represented by 'm' (where 'm' is an integer arbitrarily selected). In this case, it is possible to perform calculations while treating a direction of the dipole as an unknown parameter. Instead, it is possible to calculate using dipoles with fixed directions perpendicular to the triangular surfaces. The above setting of the direction of the dipole is made based on the physiological knowledge that the axon of the neuron existing in the cortex is roughly perpendicular to the surface of the cortex. For this reason, the present embodiment is described under a precondition that the direction of the dipole is fixed perpendicular to the surface of the triangle. Under such a precondition, the present embodiment performs estimation to obtain the magnitude of the dipole only. Of course, it is possible to perform estimation in accordance with the same method of the present embodiment under a condition where the direction of the dipole is unknown.

After completion of creation of the grid points in step 2, the system proceeds to step 3 so as to estimate dipole distribution by using the pseudoinverse. Incidentally, at a first circulation of the loop or in a state where the system does not meet the condition to get out from step 9 (which will be described later), it can be said that noise distribution has not been calculated yet. So, the aforementioned equation 13 is used for estimation of the dipole distribution q. After completion of the estimation of the dipole distribution, the system calculates a square error Ek between measured electromagnetic field distribution of y and electromagnetic field distribution which is produced by the dipole in accordance with an equation as follows:

$$f = F^+ q$$ [Equation 18]

Thereafter, the system proceeds to step 4. In the sum of the equation 13 used for the estimation of the dipole distribution in the step 3, it is possible to estimate the dipole distribution in consideration of a singular value which is obtained by performing singular value decomposition of the matrix F. For example, the sum is taken with respect to the singular values $\lambda$, such that $\lambda i/\lambda_0 > \alpha$, where $\lambda_0$ is a maximum singular value and a is a certain positive number. Thus, it is possible to avoid occurrence of divergence of the estimated values. If the estimation of the noise distribution is completed, the step 3 uses the equation 17 to estimate the magnitude of the equivalent current dipole. In consideration of the estimated noise distribution, it is possible to reduce an effect of the noise by changing the equation 13 with the equation 17 with respect to the content of the sum.

In step 4, a decision is made as to whether the noise distribution is estimated or not. In other words, the system performs checking as to whether the condition to get out from the loop is satisfied at step 9 or not. If the noise distribution is estimated, the system proceeds to step 12 to output the dipole distribution q as well as a number 'm' of the dipoles. Then, the system ends the proceeding. If the noise distribution is not estimated, the system proceeds to step 5.

In step 5, the system performs calculations of the priority order to determine a place for each of elements of the dipole distribution q which is estimated by the step 3. So, the system sorts the elements based on their places of the priority order. Herein, the sorting is performed with respect to indexes of the elements of the dipole distribution q. For example, the elements are sorted as follows:

$$(q_1, q_2, \ldots, q_i, \ldots, q_m)^T \rightarrow (q_{\pi(1)}, q_{\pi(2)}, \ldots, q_{\pi(i)}, \ldots, q_{\pi(m)})^T \quad [\text{Equation 19}]$$

where $\pi$ is a permutation operator for the sorting of the elements. Accompanied with such an operation, $F_{ij}$ (i.e., an element ij of the matrix F) is permutated by $F_{i\pi(j)}$. Thus, it is possible to execute the matrix calculations, required in the step 3, without changes at all. As the method of the sorting based on the priority order, there are provided two examples as follows:

i) The absolute value of the magnitude of the dipole is used as the place of the priority order for the sorting. Thus, the elements are sorted into an order to arrange absolute values from the highest to the lowest.

ii) A square error between measured electromagnetic field distribution and electromagnetic field distribution which is produced by a single dipole is used as the place of the priority order for the sorting. Thus, the elements are sorted into an order to arrange square errors from the lowest to the highest.

After completion of the step 5, the system proceeds to step 6. In the step 6, the system calculates an evaluation function $L_k$ based on the square error $E_k$ which is calculated in the step 4 as well as 'n' which is a number of measuring points and 'm' which is a number of dipoles. As the evaluation function $L_k$, for example, it is possible to use the equations as follows:

i) Use the structural risk defined by the aforementioned equation 16.
ii) Use the description length $L_{MDL}$ defined by a first mathematical form of equation 20.
iii) Use the Akaike information criterion $L_{AIC}$ defined by a second mathematical form of equation 20.

$$L_{MDL} = n\log E + \frac{m}{2}\log n \quad [\text{Equation 20}]$$

$$L_{AIC} = \frac{n}{2}\log E + m$$

Incidentally, the above mathematical form defining the description length $L_{MDL}$ can be assumed as a simplified form of the equation 16. By using the description length $L_{MDL}$ as the evaluation function $L_k$, it is possible to reduce an amount of calculations for the evaluation function. Incidentally, the theoretical basis for estimation of a number of parameters by using the description length is provided by "paper 5" corresponding to Rissanen, "Modeling by Shortest Data Description", Automatica, Vol. 14, pp. 465–471, 1978, for example.

In addition, the theoretical basis for estimation of a number of parameters by using the Akaike information criterion $L_{AIC}$ shown by the equation 20 is provided by "paper 6" corresponding to a book written by Mr. Ishiguro and his members which is entitled "Information Theoretical Statistics" published by Kyoritsu Publication Co. of Japan on 1983, for example.

After completion of the step 6, the system proceeds to step 7 wherein a decision is made as to whether the loop counter variable k is zero or not. If the variable k is zero, the system proceeds to step 8. If not, the system proceeds to step 9. In step 8, '1' is added to the loop counter variable k. Then, the system proceeds back to the aforementioned step 3. In step 9, the system compares the "present" evaluation function $L_k$ with a previous evaluation function $L_{k-1}$, wherein $L_k$ is produced at present execution of the loop while $L_{k-1}$ is produced at previous execution of the loop. So, a decision is made as to whether an inequality of $L_{k-1} > L_k$ is established or not. There is a tendency that a value of the evaluation function becomes small as the estimation is appropriate. So, the inequality of $L_{k-1} > L_k$ indicates that calculations of the estimation come to convergence smoothly. For this reason, under the inequality of $L_{k-1} > L_k$, the system proceeds to step 10 so as to perform estimation of the dipole distribution while changing a number of dipoles. On the other hand, an inequality of $L_{k-1} \leq L_k$ indicates that a result of the estimation is obtained for the time being. So, the system proceeds to step 11 to obtain a final result of the estimation in consideration of the effect of the noise.

In step 10, a number of dipoles is changed on the basis of the priority order which is determined by the aforementioned step 6. As the method of changing the number of the dipoles, there are provided two methods as follows:

i) Among elements of the dipole distribution q, an element of $q_{\pi(m)}$ having a smallest value is deleted, so that 'm' which is a number of dipoles is decreased by '1'.

ii) Among elements of the dipole distribution q, the system searches an element having a highest place of the priority order within a group of dipoles which are not used until now. This element is added to the dipole distribution, so that 'm' which is a number of dipoles is increased by '1'.

After changing the number of the dipoles, the system proceeds to step 8 wherein '1' is added to the loop counter variable k. Thereafter, the system proceeds back to the aforementioned step 3.

In step 11, when estimation is performed using a certain number of dipoles which brings $L_k$ to coincide with a minimum value, the square error $E_k$ is used as an estimated value of the magnitude of the noise distribution of $\|z\|$. After completion of the step 11, the system proceeds back to the step 3.

By executing the aforementioned steps, the system proceeds to step 12 at last, wherein the system outputs results of the estimation, i.e., the dipole distribution (i.e., directions and magnitude of dipoles) and a number of dipoles. Then, the system ends processing of the flowchart of FIG. 1.

Next, a description will be given with respect to results of evaluation for availability of the present invention used to perform estimation of a number of dipoles. Herein, simulation data used for the above evaluation is produced using three test dipoles. So, the method of this invention is used to perform the estimation while changing a number of model dipole(s) from one to eleven. Results of the evaluation are given by variations of an evaluation function L, which are shown in a graph of FIG. 3 wherein a vertical axis represents a value of the evaluation function L while a horizontal axis represents a number of model dipoles. Incidentally, the aforementioned structural risk is used as the evaluation function L. FIG. 3 shows that the value of the evaluation function L becomes minimal when a number of the test dipoles coincides with a number of the model dipoles. Namely, it is understood from the content of FIG. 3 that the new evaluation criterion (e.g., structural risk) employed by this invention is effective in estimation of a number of dipoles. FIG. 3 shows the case where a number of test dipoles is three. Of course, this invention is capable of estimating a number of dipoles even if a number of test dipoles is one, two or four.

Figure 4:
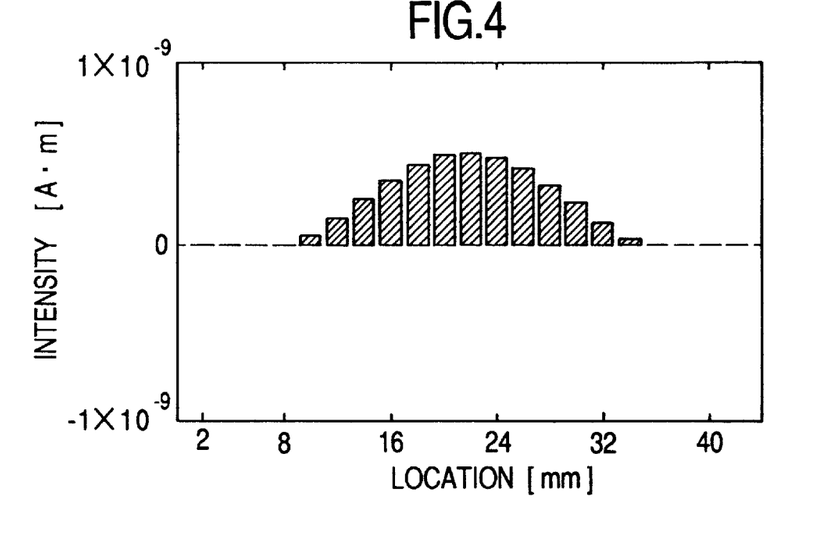
FIG. 4 is a graph showing an example of simulation data corresponding to a distributed dipole model.
Figure 5A:
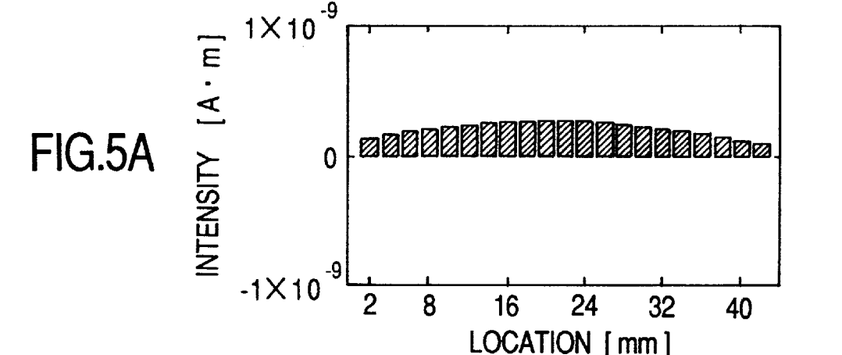
FIG. 5A is a graph showing results of estimation which is performed based on this invention with respect to the simulation data of FIG. 4.
Figure 5B:
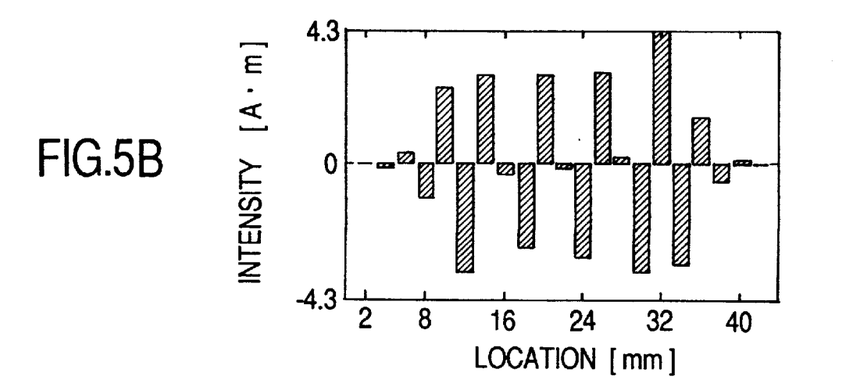
FIG. 5B is a graph showing results of estimation which is performed based on the conventional method using the pseudoinverse with respect to the simulation data of FIG. 4.

We have made another study in availability of this invention with respect to the case of the distributed active area of the brain while the noise is contained in measurement data. Herein, estimation is performed using the pseudoinverse. Simulation data subjected to the estimation are produced using a "distributed" dipole model of FIG. 4. In addition, the random noise generated on the basis of the Normal distribution is added to the simulation data, and the magnitude of the noise is set to 20% of the simulation data. Results of the estimation are shown in FIG. 5A and FIG. 5B. Specifically, FIG. 5A shows results of the estimation based on the method of this invention while FIG. 5B shows results of the estimation truly based on the conventional method using the pseudoinverse. In FIG. 4 and FIG. 5A, intensity of the equivalent current dipole (see vertical axis) is represented in an order of $\times 10^{-1}$ Angstrom-meter [A•m]. On the other hand, the intensity of the current dipole of FIG. 5B is represented in an A•m unit. So, the intensity of the equivalent current dipole of FIG. 5A differs from that of FIG. 5B by $10^{10}$ times or so. This invention is capable of detecting a center location of the original dipole distribution. In contrast, the conventional methods cannot detect a center location of the dipole distribution because the dipole distribution is affected by the noise and its estimation is subjected to divergence.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds are therefore intended to be embraced by the claims.

What is claimed is:

1. An electrophysiological activity estimation method which inputs data of measured electromagnetic field distribution measured on a surface of a living body and data of a shape of the living body so as to assume at least one equivalent current dipole in the living body as a source of the measured electromagnetic field distribution, said electrophysiological activity estimation method comprising the steps of:

performing first estimation with respect to a direction and magnitude of the equivalent current dipole such that an error between the measured electromagnetic field distribution and a theoretical value of electromagnetic field distribution caused by the equivalent current dipole becomes minimal;

determining a priority order for the estimated equivalent current dipole;

calculating an evaluation function on the basis of a number of measuring points used for measurement of the measured electromagnetic field distribution and a number of equivalent current dipoles;

changing the number of equivalent current dipoles based on the evaluation function;

performing second estimation with respect to noise distribution on the basis of the evaluation function; and outputting the direction and magnitude of the equivalent current dipole as well as the number of equivalent current dipoles.

2. An electrophysiological activity estimation method as defined in claim 1 wherein a structural risk calculated by the error, the number of measuring points and the number of equivalent current dipoles is used as the evaluation function.

3. An electrophysiological activity estimation method as defined in claim 1 wherein a description length calculated by the error, the number of measuring points and the number of equivalent current dipoles is used as the evaluation function.

4. An electrophysiological activity estimation method as defined in claim 1 wherein Akaike information criterion calculated by the error, the number of measuring points and the number of equivalent current dipoles is used as the evaluation function.

5. An electrophysiological activity estimation method as defined in claim 1 further comprising the step of:

performing deletion of equivalent current dipoles from a lowest place of the priority order.

6. An electrophysiological activity estimation method as defined in claim 1 further comprising th e step of:

performing addition of equivalent current dipoles from a highest place of the priority order.

7. An electrophysiological activity estimation method as defined in claim 1 wherein the priority order is determined using an absolute value of the equivalent current dipole.

8. An electrophysiological activity estimation method as defined in claim 1 wherein the priority order is determined using the error between the measured electromagnetic field distribution and the theoretical value of the electromagnetic field distribution caused by the equivalent current dipole.

9. An electrophysiological activity estimation method as defined in claim 1 wherein after the second estimation of the noise distribution based on the evaluation function, the first estimation is performed again in such a way that a matrix determined by position information of the equivalent current dipole and arrangement of the measuring points of the electromagnetic field distribution is subjected to singular value decomposition, so that the direction and the magnitude of the equivalent current dipole are estimated using the noise distribution as well as information of the error.

10. An electrophysiological activity estimation method as defined in claim 1 wherein the first estimation is performed in such a way that a matrix determined by position information of the equivalent current dipole and arrangement of the measuring points of the electromagnetic field distribution is subjected to singular value decomposition, so that the direction and the magnitude of the equivalent current dipole is estimated using information of a singular value.

11. An electrophysiological activity estimation method comprising the steps of:

inputting data representing measured electromagnetic field distribution which is measured at measuring points on a surface of a selected part of a living body as well as data representing a shape of the selected part of the living body;

creating grid points with respect to the surface of the selected part of the living body;

performing estimation of dipole distribution for equivalent current dipoles each of which is assumed as a source of the electromagnetic field distribution within the selected part of the living body;

determining places of a priority order with respect to the equivalent current dipoles respectively;

sorting the equivalent current dipoles in accordance with the priority order;

performing calculation to produce an evaluation function in accordance with a square error between the measured electromagnetic field distribution and a theoretical value of electromagnetic field distribution which is caused to occur due to the equivalent current dipole as well as a number of the measuring points and a number of the equivalent current dipoles; and changing the number of the equivalent current dipoles in accordance with the priority order under a condition where a result of the calculation comes to convergence, so that the aforementioned steps are repeated while changing the number of the equivalent current dipoles.

12. An electrophysiological activity estimation method as defined in claim 11 wherein the estimation is performed using a pseudoinverse while a structural risk is used as the evaluation function.

13. An electrophysiological activity estimation method as defined in claim 11 further comprising the step of:

performing estimation of noise distribution if the result of the calculation departs from the convergence, so that the dipole distribution is estimated using the noise distribution.

14. An electrophysiological activity estimation method as defined in claim 11 further comprising the step of:

performing estimation of noise distribution corresponding to a square error calculated with respect to a number of equivalent current dipoles which gives a minimum value to the evaluation function, so that the dipole distribution is estimated using the noise distribution.

15. An electrophysiological activity estimation method as defined in claim 11 wherein the dipole distribution is represented by a direction and magnitude of the equivalent current dipole as well as the number of the equivalent current dipoles which are estimated in such a way that the square error becomes minimal.

16. An electrophysiological activity estimation method as defined in claim 11 wherein the dipole distribution is represented by a direction and magnitude of the equivalent current dipole which are estimated using a singular value which are obtained by subjecting a matrix determined by a position of the equivalent current dipole and arrangement of the measuring points to singular value decomposition.

17. An electrophysiological activity estimation method as defined in claim 11 wherein the number of the equivalent current dipoles is changed in such a way that an equivalent current dipole having a smallest value within the equivalent current dipoles of the dipole distribution is deleted, so the number of the equivalent current dipoles is decreased by one.

18. An electrophysiological activity estimation method as defined in claim 11 wherein the number of the equivalent current dipoles is changed in such a way that an equivalent current dipole having a highest place of the priority order within equivalent current dipoles which are not used for the estimation is added to the dipole distribution, so the number of the equivalent current dipoles is increased by one.

19. An electrophysiological activity estimation method as defined in claim 11 wherein the selected part of the living body corresponds to a head of a human.

* * * * *